US009144634B2

(12) United States Patent
Stopek et al.

(10) Patent No.: US 9,144,634 B2
(45) Date of Patent: Sep. 29, 2015

(54) MEDICAL DEVICE WITH INTRAPORE FILMS

(75) Inventors: Joshua Stopek, Guilford, CT (US); Amin Elachchabi, Hamden, CT (US); Daniel Broom, Branford, CT (US)

(73) Assignee: Covidien LP, Mansfield, MA (US)

( * ) Notice: Subject to any disclaimer, the term of this patent is extended or adjusted under 35 U.S.C. 154(b) by 38 days.

(21) Appl. No.: 13/344,858

(22) Filed: Jan. 6, 2012

(65) Prior Publication Data

US 2012/0183583 A1 Jul. 19, 2012

Related U.S. Application Data

(60) Provisional application No. 61/432,870, filed on Jan. 14, 2011.

(51) Int. Cl.
| A61F 2/00 | (2006.01) |
| A61K 9/00 | (2006.01) |
| A61L 31/14 | (2006.01) |
| A61L 27/14 | (2006.01) |
| A61L 27/54 | (2006.01) |
| A61L 27/56 | (2006.01) |
| A61L 31/04 | (2006.01) |
| A61L 31/16 | (2006.01) |

(52) U.S. Cl.
CPC ............ *A61L 31/146* (2013.01); *A61F 2/0063* (2013.01); *A61L 27/14* (2013.01); *A61L 27/54* (2013.01); *A61L 27/56* (2013.01); *A61L 31/04* (2013.01); *A61L 31/16* (2013.01); *A61L 2300/60* (2013.01)

(58) Field of Classification Search
CPC ..... A61F 2/00; A61F 2250/0067; A61K 9/00; A61K 9/70; A61K 47/26; A61K 31/16
USPC .................. 424/400, 423, 424, 426
See application file for complete search history.

(56) References Cited

U.S. PATENT DOCUMENTS

| 3,887,699 | A | 6/1975 | Yolles |
| 4,767,628 | A | 8/1988 | Hutchinson |
| 6,264,702 | B1 | 7/2001 | Ory et al. |
| 6,270,792 | B1 | 8/2001 | Guillemet et al. |
| 6,500,777 | B1 | 12/2002 | Wiseman et al. |
| 7,041,868 | B2 | 5/2006 | Greene et al. |
| 7,252,837 | B2 | 8/2007 | Guo et al. |
| 7,279,177 | B2 | 10/2007 | Looney et al. |
| 7,556,598 | B2 | 7/2009 | Rao |
| 2002/0131988 | A1 | 9/2002 | Foster et al. |
| 2004/0098118 | A1 | 5/2004 | Granada et al. |
| 2004/0224007 | A1 | 11/2004 | Zhang |
| 2005/0244455 | A1 | 11/2005 | Greenawalt |
| 2005/0261782 | A1 | 11/2005 | Hoganson |
| 2006/0034887 | A1 | 2/2006 | Pelissier |
| 2006/0116696 | A1 | 6/2006 | Odermatt et al. |
| 2006/0121078 | A1 | 6/2006 | Trogolo et al. |
| 2006/0188546 | A1 | 8/2006 | Giroux |
| 2006/0224038 | A1 | 10/2006 | Rao |
| 2007/0129736 | A1 | 6/2007 | Solecki |
| 2007/0198040 | A1 | 8/2007 | Buevich et al. |
| 2007/0244548 | A1 | 10/2007 | Myers et al. |
| 2008/0109017 | A1 | 5/2008 | Herweck et al. |
| 2008/0113001 | A1 | 5/2008 | Herweck et al. |
| 2008/0118550 | A1 | 5/2008 | Martakos et al. |
| 2008/0199506 | A1 | 8/2008 | Horres et al. |
| 2009/0036996 | A1 | 2/2009 | Roeber |
| 2009/0142385 | A1 | 6/2009 | Gross et al. |
| 2009/0163936 | A1 | 6/2009 | Yang et al. |
| 2010/0003308 | A1 | 1/2010 | Tapolsky et al. |
| 2010/0087854 | A1* | 4/2010 | Stopek et al. ................ 606/215 |
| 2010/0089409 | A1 | 4/2010 | Bertagnoli |

FOREIGN PATENT DOCUMENTS

| EP | 2179753 A2 | 4/2010 |
| FR | 2 857 851 | 1/2005 |
| WO | WO 93/11805 | 6/1993 |
| WO | WO 02/34304 | 5/2002 |
| WO | WO 2006/020922 | 2/2006 |
| WO | WO 2006/036967 | 4/2006 |
| WO | WO 2010/093333 A1 | 8/2010 |

OTHER PUBLICATIONS

Cohen et al., Dis Colon Rectum Jun. 2005; 48(6): 1130-9. Title: Prevention of Postoperative Abdominal Adhesions by a Novel, Glycerol/Sodium Hyaluronate/Carbonxymethylcellulose-Based Bioresorbable Membrane: A Prospective, Randomized, Evaluator-Blinded Multicenter Study.
European Search Report for EP 11250641.5-2320 (3 pages) mailed Dec. 6, 2011.
Search Report from corresponding European Application No. 12151085.3 dated Jul. 15, 2013.

* cited by examiner

*Primary Examiner* — Michael G Hartley
*Assistant Examiner* — Jagadishwar Samala

(57) ABSTRACT

The present disclosure relates to a medical device and methods of making the same. The medical device includes a porous substrate and at least one film. The film is formed within the pore of the substrate. The film is intra-porous and does not contact adjacent pores or films.

18 Claims, 3 Drawing Sheets

+ BODILY FLUIDS

MEDICAL DEVICE WITH INTRAPORE FILMS

CROSS-REFERENCE TO RELATED APPLICATION

The present application claims the benefit of and priority to U.S. Provisional Application No. 61/432,870, filed on Jan. 14, 2011, the entire contents of which are incorporated by reference herein.

TECHNICAL FIELD

The present disclosure relates to medical devices, specifically those that incorporate polymeric films.

BACKGROUND

Medical devices such as implants, specifically implants having polymeric films are described in the art. Polymeric films may be used, for example, to provide strength to an implant, deliver a therapeutic agent, or enhance tissue in-growth. However, the polymeric film may increase the stiffness and reduce the handling characteristics of the implant. Additionally, the polymeric film is often uniform across the surface of the implant.

It would be advantageous to provide a medical device having a polymeric film which does not negatively impact the flexibility and handling characteristics of the medical device. It would also be advantageous to provide a medical device with a polymeric film capable of delivering varying concentrations and/or types of therapeutic agents from different segments of the medical device.

SUMMARY ACCORDING TO CLAIMS

The present disclosure provides for a medical device including a substrate including a plurality of pores, at least two of the pores include an intra-pore film disposed therein, wherein the intra-pore films are non-contiguous with respect to one another.

The present disclosure also provides for a medical device including a substrate having a first pore having a first intra-pore film disposed therein and a second pore having a second intra-pore film disposed therein, wherein the first intra-pore film and the second intra-pore film are non-contiguous with respect to one another.

A method of forming a medical device is also contemplated by the present disclosure. The method includes depositing a first film-forming composition within a first pore of a substrate; depositing a second film-forming composition within a second pore of the substrate; drying the first film-forming composition to form a first intra-pore film disposed within the first pore; and drying the second film-forming composition to form a second intra-pore film disposed within the second pore, wherein the first intra-pore film and the second intra-pore film are non-contiguous with respect to one another.

BRIEF DESCRIPTION OF DRAWINGS

Various embodiments of the present disclosure will be described herein below with reference to the figures wherein.

DETAILED DESCRIPTION

The present disclosure provides for compositions and methods of fabricating medical devices that include one or more substrates having one or more intra-pore films disposed therein. In particular, the substrate includes a plurality of pores, each of which may contain a polymeric intra-pore film. In embodiments, the medical device may include two or more substrates configured in a multi-layer structure.

Each pore of the substrate may contain one or more intra-pore films. Each intra-pore film may occupy a single pore of the substrate, thereby avoiding the stiffness that results from a continuous film. Each intra-pore film may also exhibit different degradation properties, and may be composed of similar or different materials and/or therapeutic agents which may be present at varying concentrations. In embodiments, each intra-pore film may contain different therapeutic agents depending upon the location of the pore within the substrate.

Medical devices of the present disclosure include porous substrates such as, for example, meshes, films, foams, anchors, slit sheets, stents, scaffolds, pledgets, tissue grafts (e.g., vascular, skin, bone, etc.) and the like.

In certain embodiments, the porous substrate may include a mesh. Suitable meshes for use in the present disclosure include, for example, a collagen composite mesh such as PARIETEX™ Composite Mesh (commercially available from Tyco Healthcare Group LG, d/b/a Covidien). PARIETEX™ Composite Mesh is a 3-dimensional polyester weave with a resorbable collagen film bonded on one side. Another suitable mesh includes PARIETEX PROGRIP™ self-fixating mesh (also commercially available from Covidien). PARIETEX PROGRIP™ is a polyester mesh which includes poly lactic acid (PLA) microgrips. Other suitable meshes include those sold under the names PARIETENE®, PARIETEX™, SURGIPRO™ (all commercially available from Covidien); PROLENE™ (commercially available from Ethicon, Inc.); MARLEX®, DULEX®, 3D MAX® mesh, PERFIX® plug, VENTRALEX®, and KUGEL® patch (all commercially available from C.R. Bard, Inc.); PROLITE™, PROLITE ULTRA™ (all commercially available from Atrium Medical); COMPOSIX®, SEPRAMESH®, and VISILEX® (all commercially available from Davol, Inc.); and DUALMESH®, MYCROMESH®, and INFINIT™ mesh (all commercially available from W.L. Gore). Additionally, meshes within the scope and context of this disclosure may include biologic materials such as allografts (i.e., ALLODERM® Regenerative Tissue Matrix from Lifecell), autografts, and xenografts (i.e., PERMACOL™, from Covidien). In alternate embodiments, processed/purified tissues may also be employed. Methods for making mesh are within the purview of those skilled in the art. In embodiments, PARIETEX™ Composite Mesh or PARIETEX PROGRIP™ may be utilized in accordance with the present invention.

Figure 1:
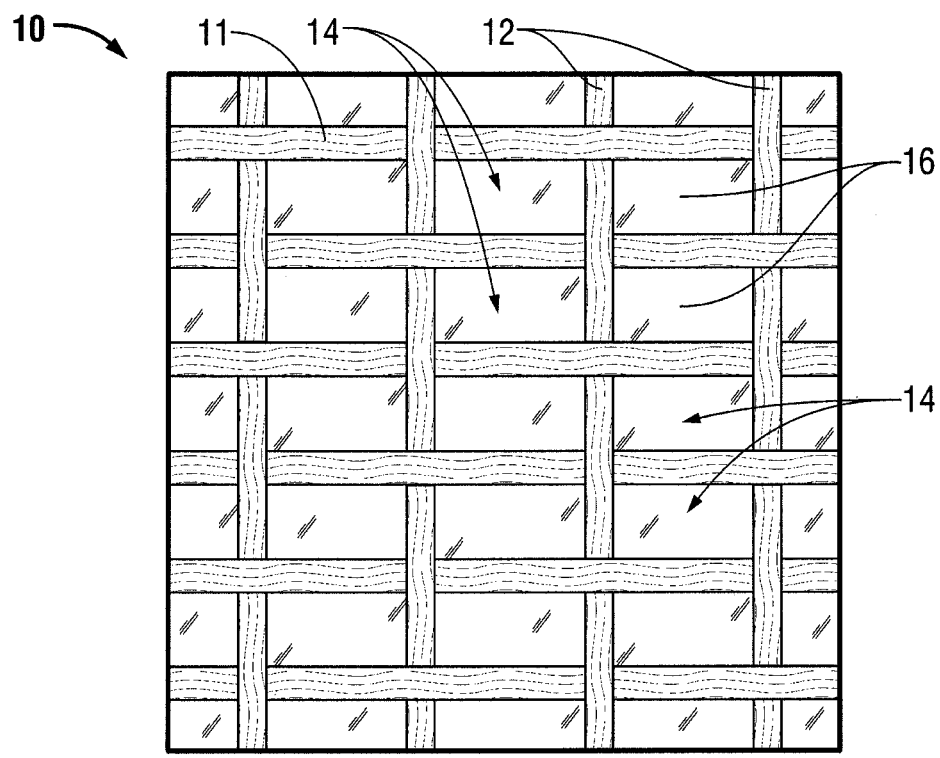
FIG. 1 shows a top view of a medical device according to an embodiment of the present disclosure.
Figure 2:
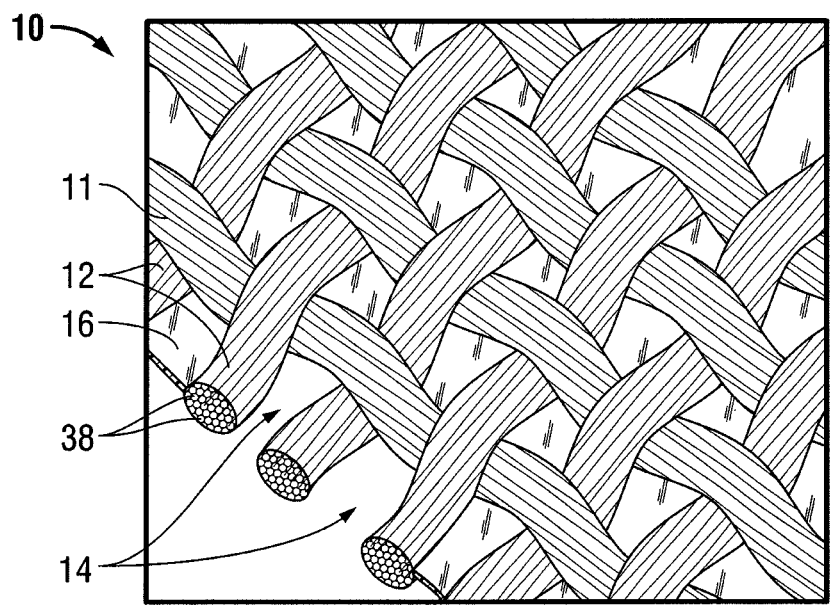
FIG. 2 shows a perspective cross-sectional view of the medical device of FIG. 1.

Turning now to FIGS. 1 and 2, a medical device 10 is illustrated including a porous mesh substrate 11. The substrate 11 may be formed from fibers, filaments, threads or yarns 12 defining a plurality of pores 14 therebetween. As shown in FIG. 2, in embodiments, the yarns 12 of the substrate 11 may be made up of multiple filaments 38. The pores 14 may include one or more intra-pore films 16. The intra-pore films 16 of the present disclosure are non-contiguous with respect to one another, with each intra-pore film 16 being located in a single pore 14 of the porous substrate 11. In embodiments, multiple intra-pore films 16 may also be formed within each of the pores 14 of the substrate 11. The term "non-contiguous" as used herein, is used to denote one or more films 16 that are contained within a corresponding pore 14 and are not in physical contact with another intra-pore film 16 of any other pore 14, as compared to a conventional film-coated porous substrate in which the film stretches across multiple pores. The intra-pore films 16 are advantageously solely/wholly contained within the pores of the substrate, that is, the intra-pore film does not span across the yarns 12 of the substrate to any substantial degree. In a further embodiment of the present invention, the intrapore film may span across the yarns of the substrate, so long as the individual films are not in physical contact with one or more intrapore films of any other pore. That is, intra-pore films 16 are non-contiguous and are not bridged together by applying a film over the entire substrate, but rather, the intra-pore films 16 are created at discrete locations, within the individual pores.

The intra-pore films 16 may be formed at any plane within the pores 14 relative to the plane of the substrate 11 such that the intra-pore film 16 does not contact any adjacent intra-pore film 16. In embodiments, the intra-pore film 16 may be textured, smooth and/or porous.

As illustrated in one embodiment of the invention described in FIG. 1, not every pore 14 may include an intra-pore film. In certain embodiments, the pores including intra-pore films may be from about 10%, 20%, 30%, 40%, 50%, 60%, 70%, 80%, 90% to about 95% of the pores. In further embodiments, about 15% to about 90% of the pores of the substrate include at least one intra-pore film. In other embodiments, from about 25% to about 75% of the pores of the substrate include at least one intra-pore film. In other embodiments, all of the pores of the substrate may include an intra-pore film.

The substrate may include at least a center and a periphery. In embodiments where less than 100% of the pores of the substrate include intra-pore films, the location of the intra-pore films may be random or patterned. For example, the pores of the substrate that include the intra-pore films may be mainly disposed in the center of the substrate or the pores that include the intra-pore films may be mainly disposed on the periphery of the substrate. In other embodiments, the location of intra-pore films may be varied (e.g., random, patterned, etc.). This may depend upon the intended use of the substrate. The intra-pore films may form a discontinuous layer covering intermittent portions of the surface of the substrate. In one example, the intra-pore films may form a discontinuous layer on the surface of the substrate, wherein the porosity of the substrate is maintained by the discontinuous layer of the intra-pore films. In a further embodiment, the intrapore films form a discontinous layer covering at least a portion of the periphery and also at a least portion of the center of the substrate.

Each intra-pore film 16 of a substrate 11 may be made from the same materials or different materials. In particular, one or more of the intra-pore films 16 may be formed from one material, while one or more different intra-pore films 16 may be formed from another material. The intra-pore film 16 may be permanent (e.g., non-bioabsorbable), biodegradable, or may be formed from any suitable combination of natural, synthetic, biodegradable and non-biodegradable materials. In the present application, the terms "biodegradable," "bioresorbable," and "bioabsorbable" are used interchangeably and are intended to mean the characteristic according to which an implant and/or a material is at least partially resorbed by biological tissues and the surrounding fluids, such that it at least partially disappears in vivo after a given period of time. The time period may vary, from about 1 minute, 2 minutes, 5 minutes, 10, 20, 30 minutes, 1 hour, 2, 6, 12, 24 hours, 2 days, 3,4,5,6 days to 1 week, 2 weeks, 4, 6 weeks to about several months or more, depending on the chemical nature of the implant and/or of the material utilized to form the implant.

In alternate embodiments, the substrate may include intra-pore films that have a varying degradation rates, such that some of the intra-pore films degrade at a rate different from that of other intra-pore films. The type of material used to form the film, concentration of the material, and structure of the film, are some factors which may affect the degradation time of the film.

Some non-limiting examples of suitable non-bioabsorbable materials which may be used to form medical devices of the present disclosure include, but are not limited to, polyolefins, such as polyethylene and polypropylene, including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof Suitable biodegradable polymers which may be used to form medical devices of the present disclosure include polymers such as aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly (hydroxybutyric acid), poly(hydroxyvaleric acid), and poly (hydroxybutyrate); polyimide carbonates; poly(imino carbonates) such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, for the purpose of this disclosure, aliphatic polyesters which may be utilized include, but are not limited to, homopolymers and copolymers of lactide (including lactic acid, D-L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α, α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable biodegradable polymers include, but are not limited to, poly(amino acids) including proteins such as collagen (I, II and III), elastin, fibrin, fibrinogen, silk, and albumin; peptides including sequences for laminin and fibronectin (especially its RGD site); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

For example, CMC may represent from about 0.1%, 0.2%, 0.5%, 1%, 2%,5%,10%,20%, 30%, 40%, 50%, 60%, 70%, 80% to about 95% (w/w)of the intra-pore films, and more particularly, from about 1% to about 75% (w/w) of the intra-pore films. In other embodiments, collagen may represent from about 0.1%, 0.2%, 0.5%, 1%, 2%,5%,10%,20%, 30%, 40%, 50%, 60%, 70%, 80% to about 95% (w/w) of the intra-pore films, more particularly, from about 1% to about 75% (w/w) of the intra-pore films.

In some cases, the intra-pore films may be formed from a film-forming composition including a film-forming polymer, and optionally a solvent and/or therapeutic agent. Suitable materials/compositions include those described herein. In particular, the film-forming composition may be a mixture, a solution, an emulsion, a suspension or any other liquid or gel containing suitable film-forming polymers. Further, suitable solvents including both polar and non-polar solvents are within the purview of those skilled in the art.

In some embodiments, the intra-pore films may include a single layer containing a hydrophobic polymer and a therapeutic agent. In other embodiments, the intra-pore films include a first layer containing a hydrophobic polymer and a second layer containing a therapeutic agent. In still other embodiments, the films include a tri-layer structure, or further layer structure wherein a second layer containing a therapeutic agent is positioned between a first layer containing a hydrophobic polymer and a third layer, or further layer containing the same or different hydrophobic polymer.

In embodiments, the hydrophobic polymers of the intra-pore films may include homopolymers or copolymers of lactide, glycolide, dioxanone, trimethylene carbonate, and ε-caprolactone. For example, the therapeutic agents described herein may be combined with copolymers, i.e., random, or block copolymers, of lactide and glycolide or glycolide and ε-caprolactone.

Figure 3:
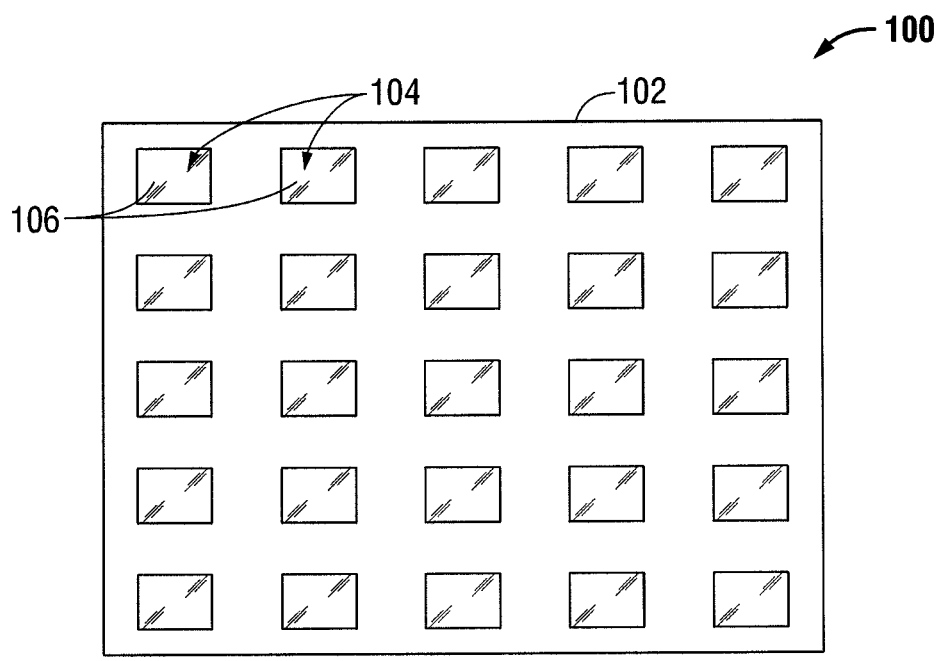
FIG. 3 shows a top view of a medical device according to an embodiment of the present disclosure.

FIG. 3 describes a specific embodiment of the invention. In particular, it shows a medical device 100 having a substrate 102. In embodiments, the substrate 102 may be a polysaccharide or lactone based scaffold. The substrate 102 may be made from non-denatured collagen, or collagen which has at least partially lost its helical structure through heating or any other known method so it primarily possesses non-hydrolyzed alpha chains, and having a molecular weight, in embodiments, of about 100 kDa. The collagen may be native collagen or atelocollagen, which may be obtained via pepsin digestion and/or after moderate heating.

The substrate 102 may be formed from a collagen suspension or solution of non-cured, moderately cured, highly cured, or extremely highly cured collagens, or combinations thereof, at any proportion. As used herein, the term "moderately cured" is intended to mean that the degradation of the substrate 102 will be at least about 90% complete (as measured by residual weight) by the end of about three weeks of implantation; the term "highly cured" is intended to mean that the degradation of the substrate 102 will be at least about 90% complete (as measured by residual weight) by the end of about three months of implantation; and the term "extremely highly cured" is intended to mean that the degradation of the substrate 102 will be at least about 90% complete (as measured by residual weight) by the end of about two years of implantation.

Moderately cured collagen may be obtained by oxidative cleavage of collagen by periodic acid or one of its salts. In embodiments, highly cured collagen may be made from collagen cross-linked by glutaraldehyde or by any other known cross-linking agents such as, for example, isocyanates. The degree of crosslinking distinguishes between highly cured and very highly cured materials. Techniques for curing to various degrees are within the purview of those skilled in the art.

The substrate 102 includes a plurality of depots or pores 104. The pores 104 may be disposed on a surface of the substrate 102 or may, in part at least pass through the substrate 102. In one embodiment of the invention, the pores pass completely through the substrate. The pores 104, may be evenly spaced through the surface of the substrate 102. In embodiments, the distance between the pores 104 may be substantially equal to the dimensions (e.g., length and width) of the pores 104. In particular, the lengthwise separation between the pores 104 may be substantially equal to the length of the pores 104 and the widthwise separation between the pores 104 may be substantially equal to the width of the pores 104.

Each of the pores 104 includes intra-pore films 106 which are substantially similar to the intra-pore films 16 of FIGS. 1 and 2. The films 106 may be formed utilizing methods described herein.

Figure 4A:
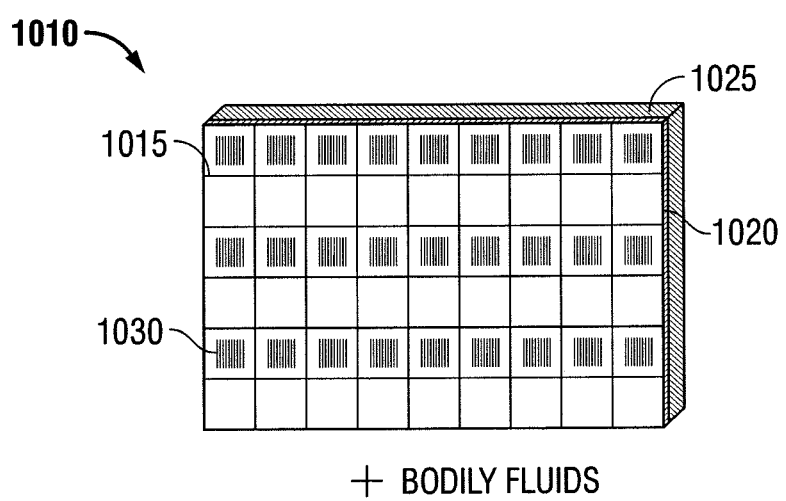
FIGS. 4A-4C are perspective views of a medical device according to an embodiment of the present disclosure.
Figure 4B:
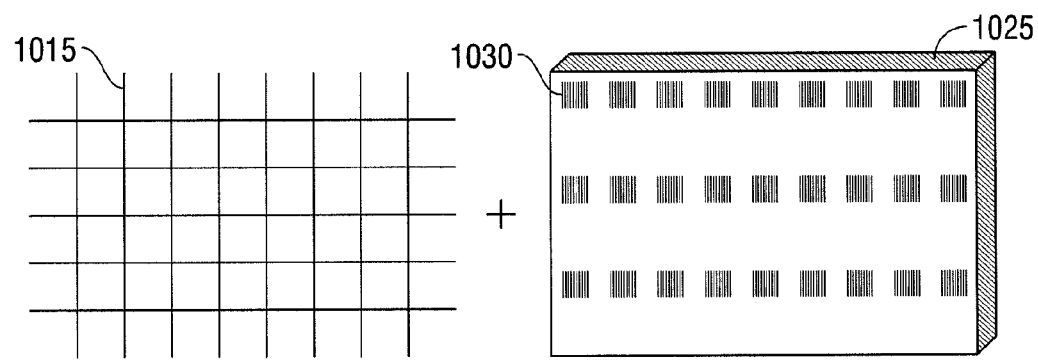
Figure 4C:
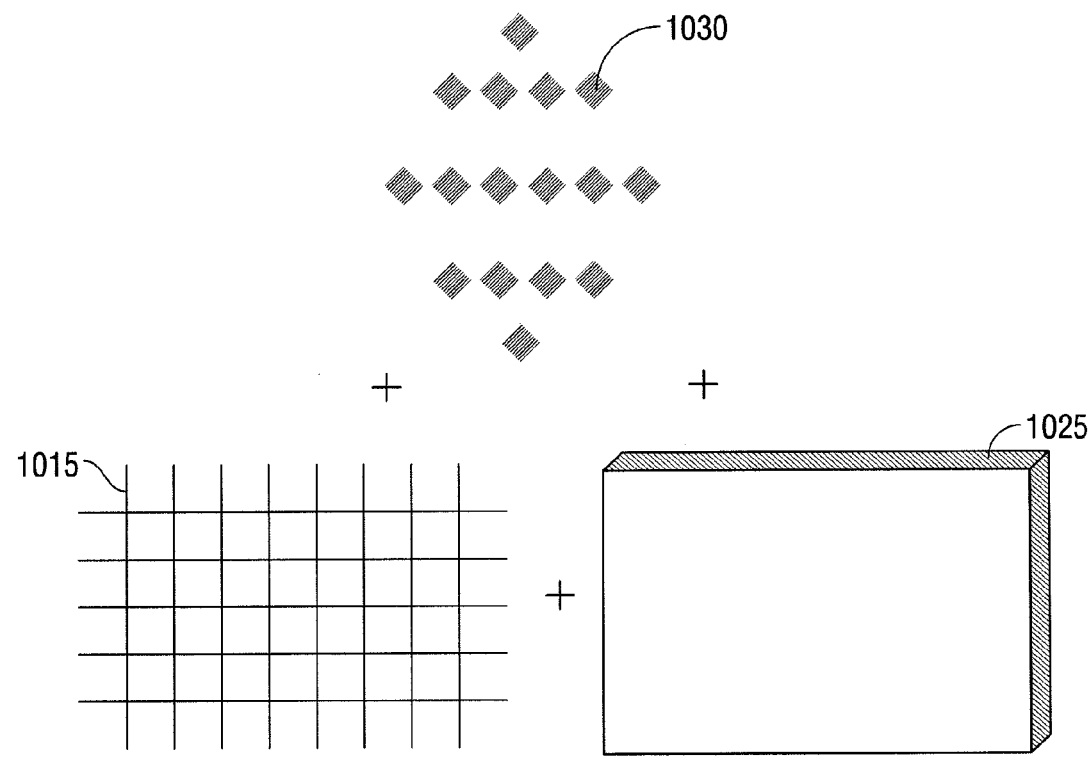

As depicted in FIGS. 4A, 4B and 4C, the medical device 1010 includes a porous substrate 1015, a detachable layer 1020 disposed between the substrate 1015 and a polymeric film layer 1025, and one or more therapeutic agents 1030. The porous substrate 1015 may be substantially similar to the substrates 11 and 102 described above with respect to FIGS. 1-3. The porous substrate 1015 may include a plurality of pores and may include a plurality of intra-pore components (e.g., films) that are disposed within the pores of the substrate 1015 as discussed above with respect to FIGS. 1-3. Therapeutic agents 1030 may be disposed within any of the components of the medical device 1010 including the porous substrate 1015 (e.g., within intra-pore films), the detachable layer 1020, and the polymeric film layer 1025.

Following implantation of the medical device 1010 and/or exposure to bodily fluids, including water, blood, mucous, saline, dextrose and the like, the detachable layer 1020 undergoes degradation and/or dissolution, e.g., the detachable layer 1020 may be reduced from a solid or gel to a liquid following interaction with bodily fluids located at the site of implantation thereby separating the polymeric film layer 1025 from the substrate 1015. In embodiments, the polymeric film layer 1025 may be positioned adjacent only the detachable layer 1020. In such embodiments, dissolution of the detachable layer 1020 allows for the complete release or detachment of the polymeric film layer 1025 from the substrate 1015.

Detachable layer 1020 may hydrate and dissolve into the bodily fluids detaching polymeric film layer 1025 along with therapeutic agent 1030 from substrate 1015 to create multiple, separate implantable medical devices, i.e., a substrate 1015 and a film 1025 for delivery of therapeutic agents 1030, as shown in FIG. 4B. Over time, film 1025 will degrade and/or dissolve, releasing therapeutic agent 1030 from the film 1025 and the substrate 1015 as shown in FIG. 4C.

In alternate embodiments, the intra-pore films may include a hydrogel. Upon implantation and uptake of bodily fluids and/or water or saline, the hydrogel may swell and detach from the surface of the medical device and/or the polymeric layer. Upon detachment, the intra-pore films are released from contact with the surface of the substrate. Suitable hydrogels may include bioabsorbable polymers such as those listed herein.

Medical devices of the present disclosure may be prepared by applying the film-forming composition (e.g., sprayed) to at least one pore of the substrate and allowed to dry. Each pore may be individually provided with an intra-pore film by repeating this process. In embodiments, the film-forming polymer composition may be applied into the pore of the substrate at various angles, adjusting the surface of the mold or template to accommodate the substrate. Certain techniques, such as ultrasonic spray coating enables the application of intra-pore films at precise locations, within the pores or the substrate. Additionally, these techniques may accommodate various geometrical constraints of implants and may be employed with the pores having an area from about 100, 200, 500, 1000 square microns to about 15 square millimeters (mm). As previously discussed, the intra-pore films may also include several layers of films, creating a multilayer, intra-pore film.

The film-forming composition may be created through use of a spraying process, for example, ultrasonic spraying. Ultrasonically spraying films results in a unique ability to place a high therapeutic payload of a therapeutic agent within the pores. For example, the medical device as described herein may be fabricated by passing a first solution containing a hydrophobic polymer and a second solution containing a therapeutic agent through an ultrasonic spray nozzle to form droplets. The droplets may be mixed while falling towards or being deposited onto an inert substrate, such as a silicone sheet, or the detachable layer of a medical device to form a film.

Alternatively, the intra-pore films may be created using a template and later combined with the substrate utilizing solvents, adhesives or welding. Intra-pore films may also be created using masking techniques, where a portion of the substrate is masked or shielded and the film is then applied to the substrate and exposed or unmasked pores. The mask is then removed, yielding intra-pore films, disposed at discrete, precise locations within the pores.

The intra-pore films may be designed to dissolve within a particular period of time. For example, the intra-pore films may be designed to dissolve within less than 96 hours after implantation. In some embodiments, the intra-pore films may dissolve within a time from about 5, 10, 20, 30 seconds, 1 minute, 2, 5,10, 20, 30 minutes, 1 hour, 2 hours, 6 hours, 12 hours to about 24 hours following implantation. In certain embodiments, the intra-pore films may dissolve within a time from about 30 seconds to about 12 hours following implantation.

Both the substrate and the intra-pore films may also include one or more optional ingredients. Some examples of suitable optional ingredients include emulsifiers, viscosity enhancers, dyes, pigments, fragrances, pH modifiers, wetting agents, plasticizers, antioxidants, combination thereof, and the like. The optional ingredients may represent about 1%, 2%, 3%, 4%, 5%, 6%, 7%, 8% up to about 10% of the intra-pore films and/or polymeric layer by weight.

In some embodiments, the intra-pore films may include at least one plasticizer, e.g., glycerol. For instance, the intra-pore films may include a combination of CMC and glycerol to form detachable intra-pore films as discussed herein.

The pores and intra-pore films may have an area from about 100 square microns to about 15 square mm. In embodiments, the pores and intra-pore films may have an area from about 1, 2, 3, 4, 5,6,7,8 square mm to about 10 square mm. In other embodiments, the pores and intra-pore films may have an area from about 3 square mm to about 5 square mm. It should be understood that the area may be calculated by different methods depending on the geometry of the pores (e.g., circular pores have an area of $\pi r^2$, whereas a rectangular pore may be calculated using its length and width, etc.).

The medical device, including the substrate and intra-pore films, may also include a therapeutic agent. Each component of the medical device may include a therapeutic agent, namely the substrate and the intra-pore films. The concentration and type of therapeutic agent may be the same or different in each component (e.g., intra-pore film and/or in the substrate). The concentration of the therapeutic agent and the degradation rate of the intra-pore films and or substrate may be modified so as to provide specific release rates of the therapeutic agents.

In embodiments, an intra-pore film in one portion of the substrate may contain a therapeutic agent specific to its location within the substrate. For example, a portion of the substrate contacting a wound may include one or more intra-pore films containing a hemostatic and/or analgesic agent, while intra-pore films located in a portion of the substrate contacting healthy tissue may contain an anti-adhesive agent. In embodiments, the pores at the center of the substrate may include a therapeutic agent, while the pores of the substrate located on the periphery may not include a therapeutic agent, or vice versa.

The term "therapeutic agent," as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic effect, such as, anti-adhesives, antimicrobials, analgesics, antipyretics, anesthetics (e.g. local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, chemotherapeutics, anticancer agents, immunogenic agents, immunosuppressants, drugs acting on the gastrointestinal system, diuretics, steroids, lipids, lipopolysaccharides, polysaccharides, platelet activating drugs, clotting factors, and enzymes. It is also intended that combinations of agents may be used.

Therapeutic agents include, but are not limited to, drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, and ribozymes.

In embodiments, the therapeutic agent may include at least one of the following drugs, including combinations and alternative forms of the drugs such as alternative salt forms, free acid form, free base forms, pro-drugs and hydrates: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydchloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, capsaicin and meprobamate); local anesthetic agents (e.g., lidocaine, bupivacaine, ropivacaine and levobupivacaine); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconazole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone); antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate; steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, glipizide, tolbutamide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. In some embodiments, the therapeutic agent may be water soluble. In some embodiments, the therapeutic agent may not be water soluble.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

We claim:

1. A medical device comprising:
a substrate including a plurality of pores, at least two, adjacent pores of the plurality of pores including an intra-pore film disposed therein, wherein the intra-pore films are non-contiguous with respect to one another and are fully contained within each of the at least two, adjacent pores, the intra-pore film disposed in one of the at least two, adjacent pores having a first degradation rate and the intra-pore film disposed in the other of the at least two, adjacent pores having a second degradation rate different from the first degradation rate.

2. The medical device according to claim 1, wherein the substrate comprises a mesh including a plurality of yarns defining the plurality of pores therebetween.

3. The medical device according to claim 1, wherein the intra-pore films are separated by a yarn that is in communication with each of the at least two, adjacent pores.

4. The medical device according to claim 1, wherein the substrate is selected from the group consisting of a foam, an anchor, a slit sheet, a stent, a scaffold, a pledget, and a tissue graft.

5. The medical device according to claim 1, wherein the intra-pore films have an area from about 100 square microns to about 15 square millimeters.

6. The medical device according to claim 5, wherein the area of each of the intra-pore films is from about 1 square millimeter to about 10 square millimeters.

7. The medical device according to claim 6, wherein the area of each of the intra-pore films is from about 3 square millimeters to about 5 square millimeters.

8. The medical device according to claim 1, wherein the intra-pore films include at least one polymer selected from the group consisting of absorbable polymers and non-absorbable polymers.

9. The medical device according to claim 1, wherein the intra-pore films are formed from at least one biodegradable polymer selected from the group consisting of polysaccharides, polylactones, vinyl polymers, and combinations thereof.

10. The medical device according to claim 1, further comprising a therapeutic agent selected from the group consisting of an analgesic agent, an anesthetic agent, an antibiotic agent, an antimicrobial agent, an anticoagulant agent, a hemostatic agent, and combinations thereof.

11. The medical device according to claim 1, wherein from about 10% to about 100% of the plurality of pores include at least one intra-pore film disposed therein.

12. The medical device according to claim 1, wherein the substrate has a top surface defining a first plane and a bottom surface defining a second plane, an entirety of the intra-pore films disposed between the first and second planes.

13. A medical device comprising:
a substrate including:
a first pore having a first intra-pore film disposed only within the first pore, the first intra-pore film having a first degradation rate; and
a second pore disposed adjacent to the first pore and having a second intra-pore film disposed only within the second pore, the second intra-pore film having a second degradation rate different from the first degradation rate, wherein the first intra-pore film and the second intra-pore film are non-contiguous with respect to one another.

14. The medical device according to claim 13, further comprising at least one therapeutic agent selected from the group consisting of an analgesic agent, an anesthetic agent, an antibiotic agent, an antimicrobial agent, an anticoagulant agent, a hemostatic agent, and combinations thereof.

15. The medical device according to claim 14, wherein the first intra-pore film and the second intra-pore film include the at least one therapeutic agent at different concentrations.

16. The medical device according to claim 13, wherein the first intra-pore film and the second intra-pore film comprise different materials.

17. The medical device according to claim 13, wherein the first and second intra-pore films are separated by a yarn that is in communication with each of the first and second pores.

18. The medical device according to claim 13, wherein the substrate has a top surface defining a first plane and a bottom surface defining a second plane, an entirety of the intra-pore films disposed between the first and second planes.

* * * * *